United States Patent
Cho et al.

(10) Patent No.: US 9,832,370 B2
(45) Date of Patent: Nov. 28, 2017

(54) COGNITIVE SENSOR AND METHOD OF OPERATING OF THE SAME

(71) Applicant: Samsung Electronics Co., Ltd., Suwon-si, Gyeonggi-do (KR)

(72) Inventors: Seongho Cho, Gwacheon-si (KR); Youngsoo Park, Yongin-si (KR); Euichul Hwang, Seongnam-si (KR); Myoungjae Lee, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 4 days.

(21) Appl. No.: 14/802,315

(22) Filed: Jul. 17, 2015

(65) Prior Publication Data
US 2016/0021302 A1 Jan. 21, 2016

(30) Foreign Application Priority Data
Jul. 18, 2014 (KR) ........................ 10-2014-0091309

(51) Int. Cl.
| | |
|---|---|
| *H04N 5/228* | (2006.01) |
| *H04N 5/232* | (2006.01) |
| *A61B 5/00* | (2006.01) |
| *H04N 5/345* | (2011.01) |
| *A61B 3/113* | (2006.01) |
| *A61B 8/08* | (2006.01) |
| *A61B 5/11* | (2006.01) |

(52) U.S. Cl.
CPC ....... *H04N 5/23219* (2013.01); *A61B 5/0037* (2013.01); *H04N 5/3454* (2013.01); *A61B 3/113* (2013.01); *A61B 5/11* (2013.01); *A61B 8/5207* (2013.01); *A61B 2576/00* (2013.01)

(58) Field of Classification Search
CPC .......... H04N 5/23222; H04N 5/23219; H04N 5/23212; A61B 5/0037; A61B 2576/00; A61B 5/11; A61B 8/5207; A61B 3/113
USPC ...................................... 348/222.1
See application file for complete search history.

(56) References Cited

U.S. PATENT DOCUMENTS

| | | | |
|---|---|---|---|
| 8,478,081 B2 | 7/2013 | Paillet et al. | |
| 2003/0085336 A1* | 5/2003 | Wu ........................ | G06K 9/60 250/208.1 |
| 2009/0066782 A1* | 3/2009 | Choi ..................... | H04N 3/155 348/25 |
| 2009/0097704 A1* | 4/2009 | Savidge .................. | G06K 9/32 382/103 |

(Continued)

FOREIGN PATENT DOCUMENTS

JP  5310076 B2  10/2013

*Primary Examiner* — Yogesh Aggarwal
(74) *Attorney, Agent, or Firm* — Harness, Dickey & Pierce P.L.C.

(57) ABSTRACT

A cognitive sensor and a method of operating the same. The cognitive sensor includes a sensor unit, which generates electric signals in response to outside stimulations; a signal processing unit, which generates sensed data regarding the outside stimulations by processing electric signals generated by the sensor unit; a cognitive circuit unit, which specifies an area of interest in the sensed data processed by the signal processing unit; and an output unit, which outputs the sensed data generated by the signal processing unit, wherein at least a portion of the sensed data output by the output unit is sensed data regarding the area of interest.

18 Claims, 8 Drawing Sheets

(56) References Cited

U.S. PATENT DOCUMENTS

2012/0105668 A1 5/2012 Velarde et al.
2013/0245422 A1 9/2013 D'arcy et al.

* cited by examiner

COGNITIVE SENSOR AND METHOD OF OPERATING OF THE SAME

RELATED APPLICATION

This application claims the benefit of priority from Korean Patent Application No. 10-2014-0091309, filed on Jul. 18, 2014, in the Korean Intellectual Property Office, the disclosure of which is incorporated herein in its entirety by reference.

BACKGROUND

1. Field

Example embodiments relate to sensors for detecting outside stimulations, and more particularly, to cognitive sensors, and/or methods of operating the same.

2. Description of the Related Art

Sensors are typically categorized in five classes (sight, hearing, smell, taste, and touch) of sensors, biosensors for sensing blood sugar, blood pressure, body fat, cholesterol, etc., and environmental sensors for sensing various chemical substances.

Such a sensor may be embodied as a chip including a sensor unit for converting outside stimulations into electric signals, a signal processing circuit for processing electric signals converted by the sensor unit, and an input/output (I/O) circuit. For example, a CMOS image sensor may be a semiconductor chip including a pixel array in which photoelectric conversion units are 2-dimensionally arranged, a control unit for controlling the pixel array, a readout circuit for reading out pixel signals output from the pixel array, and an image signal processing unit for processing the pixel signals read out by the readout circuit into an image.

Meanwhile, an information processing system that processes sensed data obtained via a sensor typically uses artificial intelligence (AI) for extracting relevant information from the sensed data. For example, a method of extracting human faces from a photographic image including both humans and landscapes by using an AI technology has been suggested, and such a method is applied to a focusing algorithm for picking up portrait images in a camera.

When an amount of signal data increases, a sensor in the related art typically exhibits large power consumption and slow processing speed for processing signals. For example, in the case of an image sensor, as the number of pixel increases, the image sensor exhibits large power consumption and slow processing speed for processing an image. Furthermore, an information processing apparatus in the related art receives all of the sensed data sensed by a sensor and processes the sensed data. Therefore, as the number of sensing elements of a sensor increases, an amount of raw data transmitted from the sensor increases. As a result, a bottleneck phenomenon may take place during data transmission from the sensor to the information processing apparatus, and the information processing apparatus also typically exhibits large power consumption and slow processing speed for processing signals.

SUMMARY

Example embodiments relate to cognitive sensors and methods of operating the same.

Additional example embodiments will be set forth in part in the description which follows and, in part, will be apparent from the description, or may be learned by practice of the example embodiments.

According to at least one example embodiment, a cognitive sensor includes a sensor unit configured to generate electric signals in response to outside stimulations, a signal processing unit configured to generate sensed data regarding the outside stimulations by processing electric signals generated by the sensor unit, a cognitive circuit unit configured to specify an area of interest in the sensed data processed by the signal processing unit, and an output unit configured to output the sensed data generated by the signal processing unit, wherein at least a portion of the sensed data output by the output unit is sensed data regarding the area of interest.

According to at least one example embodiment, the sensor unit, the signal processing unit, the cognitive circuit unit, and the output unit are integrated on a single chip.

The signal processing unit may be configured to replace data corresponding to areas other than the area of interest in the sensed data regarding the area of interest with existing data, null data, dummy data, or low-resolution data.

The sensor unit is a sensing element array having arranged therein a plurality of sensing elements, each of which may be configured to convert outside stimulations into electric signals.

The signal processing unit may be configured to generate sensed data regarding outside stimulations corresponding to the area of interest by processing electric signals obtained from the sensing elements corresponding to the area of interest from among the plurality of sensing elements, based on the area of interest specified by the cognitive circuit unit.

The cognitive sensor further includes a driving circuit unit configured to drive the sensing element array, wherein the driving circuit unit selectively drives sensing elements corresponding to the area of interest from among the plurality of sensing elements, based on information regarding the area of interest received from the cognitive circuit unit.

While sensed data regarding outside stimulations corresponding to the area of interest is being generated, the driving circuit unit drives only sensing elements corresponding to the area of interest from among the plurality of sensing elements and does not drive the other sensing elements.

Each of the plurality of sensing elements includes a photoelectric conversion element configured to convert a light into electric signals.

The sensor unit is one from among an ultrasound transducer configured to convert an ultrasound wave into electric signals, a tactile sensor configured to sense contact of a target object, a pressure sensor configured to sense a pressure from a target object, a bio-sensor configured to sense biological substances, and a chemical substance sensor configured to sense chemical substances.

The cognitive circuit unit may be a neural network circuit or a neuromorphic circuit.

The cognitive circuit unit specifies an area of interest in sensed data detected by the sensor unit based on educated information.

The outside stimulation may be one from among an electromagnetic wave, a sound wave, a contact, a pressure, a biological substance, or a chemical substance.

According to another example embodiment, a recognizing apparatus includes a cognitive sensor as described above and a second sensor configured to obtain initial information for specifying an area of interest, wherein a cognitive circuit unit of the cognitive sensor specifies an area of interest based on information obtained via the second sensor.

The second sensor may be an eye-tracking sensor or a motion sensor.

According to another example embodiment, a recognizing apparatus includes a cognitive sensor including a sensor unit configured to generate electric signals in response to outside stimulations, a signal processing unit configured to generate sensed data regarding the outside stimulations by processing electric signals generated by the sensor unit, a cognitive circuit unit configured to specify an area of interest in the sensed data processed by the signal processing unit, and an output unit configured to output the sensed data generated by the signal processing unit, wherein at least a portion of the sensed data output by the output unit is sensed data regarding the area of interest, and a computing device, to which the cognitive sensor is connected via a network, wherein the cognitive circuit unit of the cognitive sensor specifies an area of interest in conjunction with the computing device.

According to at least one example embodiment, a method of operating a cognitive sensor, which includes a sensor unit, which generates electric signals in response to outside stimulations, a signal processing unit, which generates sensed data regarding the outside stimulations by processing electric signals generated by the sensor unit, a cognitive circuit unit, which specifies an area of interest in the sensed data processed by the signal processing unit, and an output unit, which outputs the sensed data generated by the signal processing unit, the method includes converting an outside stimulation into electric signals at the sensor unit, specifying an area of interest by using the cognitive circuit unit, generating sensed data regarding the area of interest by processing electric signals corresponding to the area of interest from among the electric signals converted by the sensor unit at the signal processing unit, and outputting the sensed data generated by the signal processing unit via an I/O unit, wherein at least a portion of the sensed data output by the output unit is sensed data regarding the area of interest.

According to at least one example embodiment, the signal processing unit is configured to replace data corresponding to areas other than the area of interest in the sensed data regarding the area of interest with existing data, null data, dummy data, or low-resolution data.

The specifying of the area of interest may be periodically performed.

The method further includes recognizing a change of situation, wherein an area of interest is re-specified based on information regarding a cognized change of situation.

The sensor unit is a sensing element array having arranged therein a plurality of sensing elements each of which configured to convert outside stimulations into electric signals, and sensing elements corresponding to the area of interest from among the plurality of sensing elements are selectively driven, based on information regarding the area of interest received from the cognitive circuit unit

BRIEF DESCRIPTION OF THE DRAWINGS

These and/or other example embodiments will become apparent and more readily appreciated from the following description of the example embodiments, taken in conjunction with the accompanying drawings in which.

DETAILED DESCRIPTION

Figure 1:
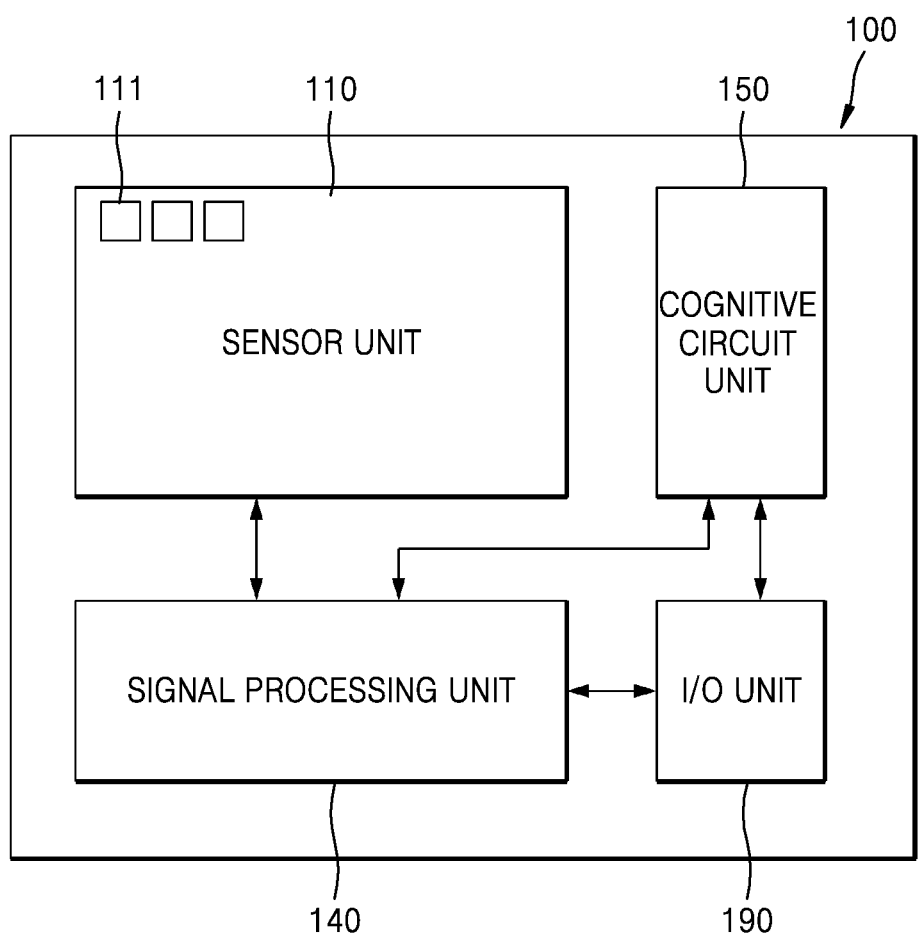
FIG. 1 is a schematic block diagram showing a cognitive sensor according to an example embodiment.

The example embodiments are described more fully with reference to the accompanying drawings. The example embodiments may, however, be embodied in many different forms and should not be construed as being limited to the example embodiments set forth herein; rather, these example embodiments are provided so that this disclosure will be thorough and complete, and will fully convey the concepts of the invention to those skilled in the art. In the drawings, the thicknesses of layers and regions are exaggerated for clarity. Like reference numerals in the drawings denote like elements, and thus their description will be omitted.

In addition, although the terms used in the example embodiments are selected from generally known and used terms, some of the terms mentioned in the description of the example embodiments have been selected by the applicant at his or her discretion, the detailed meanings of which are described in relevant parts of the description herein. Furthermore, the example embodiments should be understood, not simply by the actual terms used but by the meaning of each term lying within.

It will be understood that although the terms "first" and "second" are used herein to describe various elements, these elements should not be limited by these terms. These terms are only used to distinguish one element from another element. Thus, a first element discussed below could be termed a second element, and similarly, a second element may be termed a first element without departing from the teachings of this disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present. Other expressions for describing relationships between components, such as "between ~ and ~" and "directly between ~ and ~" or "next to ~" and "directly next to ~" should be understood in the same regard.

In the drawing figures, the dimensions of layers and regions may be exaggerated for clarity of illustration. Like reference numerals refer to like elements throughout. The same reference numbers indicate the same components throughout the specification.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

Reference will now be made in detail to example embodiments, examples of which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain the example description.

FIG. 1 is a schematic block diagram showing a cognitive sensor 100 according to an example embodiment.

Referring to FIG. 1, the cognitive sensor 100 includes a sensor unit 110, a signal processing unit 140, a cognitive circuit unit 150, and an input/output (I/O) unit 190.

The sensor unit 110 includes an area reacting with outside stimulation. The sensor unit 110 may be a sensing element array in which a plurality of sensing elements 111 are spatially arranged. The plurality of sensing elements 111 may be arranged in a matrix shape, that is, 2-dimensionally arranged. As another example, the plurality of sensing elements 111 may be linearly arranged, that is, 1-dimensionally arranged. As the plurality of sensing elements 111 are spatially arranged, the sensor unit 110 may obtain information regarding outside stimulation as a spatial image.

According to at least one example embodiment, each of the plurality of sensing elements 111 generates an electric signal in response to an outside stimulation. Outside stimulations to which the plurality of sensing elements 111 react may include electromagnetic waves, such as visible rays, infrared rays, X-rays, gamma rays, etc. For example, the sensing elements 111 may include photoelectric conversion elements known in the art for converting light into electric signals. The photoelectric conversion element may be a photodiode or a photoconductor. For another example, outside stimulations may include acoustic waves, ultrasound waves, contacts, pressure, biologic substances, chemical substances, and the like. For example, the sensing elements 111 may be ultrasound transducer for converting ultrasound waves into electric signals, tactile sensors for detecting contacts of target objects, pressure sensors for detecting pressures from target objects, biosensors for detecting biological substances, or chemical sensors for detecting chemical substances.

The signal processing unit 140 may be a circuit configured to generate sensed data regarding outside stimulations by processing electric signals transmitted from the sensor unit 110. For example, if the sensing elements 111 are photoelectric conversion devices, sensed data generated by the signal processing unit 140 may be a still image or a moving picture. For another example, if the sensing elements 111 are ultrasound transducers, sensed data generated by the signal processing unit 140 may be an ultrasound image.

The signal processing unit 140 may be configured to receive electric signals from some of, or the entire plurality of, sensing elements 111 regularly or irregularly, may be configured to generate all-area sensed data, and may be configured to transmit the all-area sensed data to the cognitive circuit unit 150. Here, the all-area sensed data refers to data obtained from a portion of or the entire plurality of sensing elements 111, that is, an entire sensor area of the sensor unit 110. Furthermore, as described below, the signal processing unit 140 may be configured to generate sensed data corresponding to an area of interest based on information regarding the area of interest specified by the cognitive circuit unit 150. Sensed data corresponding to an area of interest is referred to as area of interest sensed data.

The cognitive circuit unit 150 may be configured to specify an area of interest based on all-area sensed data transmitted from the signal processing unit 140. The cognitive circuit unit 150 may be embodied based on artificial intelligence technologies known in the art. For example, the cognitive circuit unit 150 may be a neural network, such as a digital convolution neural network (CNN) or an analog-like/analog CNN, or a neuromorphic circuit, such as a Spike neuromorphic circuit or a rate neuromorphic circuit.

An example area of interest refers to an area including an object or information interested by a user in all-area sensed data. The cognitive circuit unit 150 may be configured to be trained in advance for specification of an area of interest in all-area sensed data through machine learning. For example, if all-area sensed data regarding outside stimulations obtained via the plurality of sensing elements 111 of the sensor unit 110 include an image of various objects, an area of interest may be an area in which a particular object is located in the image, and the cognitive circuit unit 150 may be configured to be trained in advance for extracting the particular object from among the various objects in the image. Information regarding particular objects to extract (e.g., feature points of objects) may be stored in a memory (not shown) in advance, and the cognitive circuit unit 150 may refer to the information stored in the memory.

The I/O unit 190 may be configured to output sensed data generated by the signal processing unit 140. Control signals regarding the cognitive sensor 100 or information or programs for the cognitive circuit unit 150 to specify an area of interest may be input via the I/O unit 190. The I/O unit 190 may include an input unit and an output unit that are integrated with each other circuit-wise, or separated from each other.

The sensor unit 110, the signal processing unit 140, the cognitive circuit unit 150, and the I/O unit 190 as described above may be integrated on a single chip. The sensor unit 110, the signal processing unit 140, the cognitive circuit unit 150, and the I/O unit 190 may be fabricated on a single wafer at once during a semiconductor fabrication process, or may be separately fabricated and integrated on a single chip.

Next, a method of operating the cognitive sensor 100 according to at least one example embodiment will be described.

Figure 2:
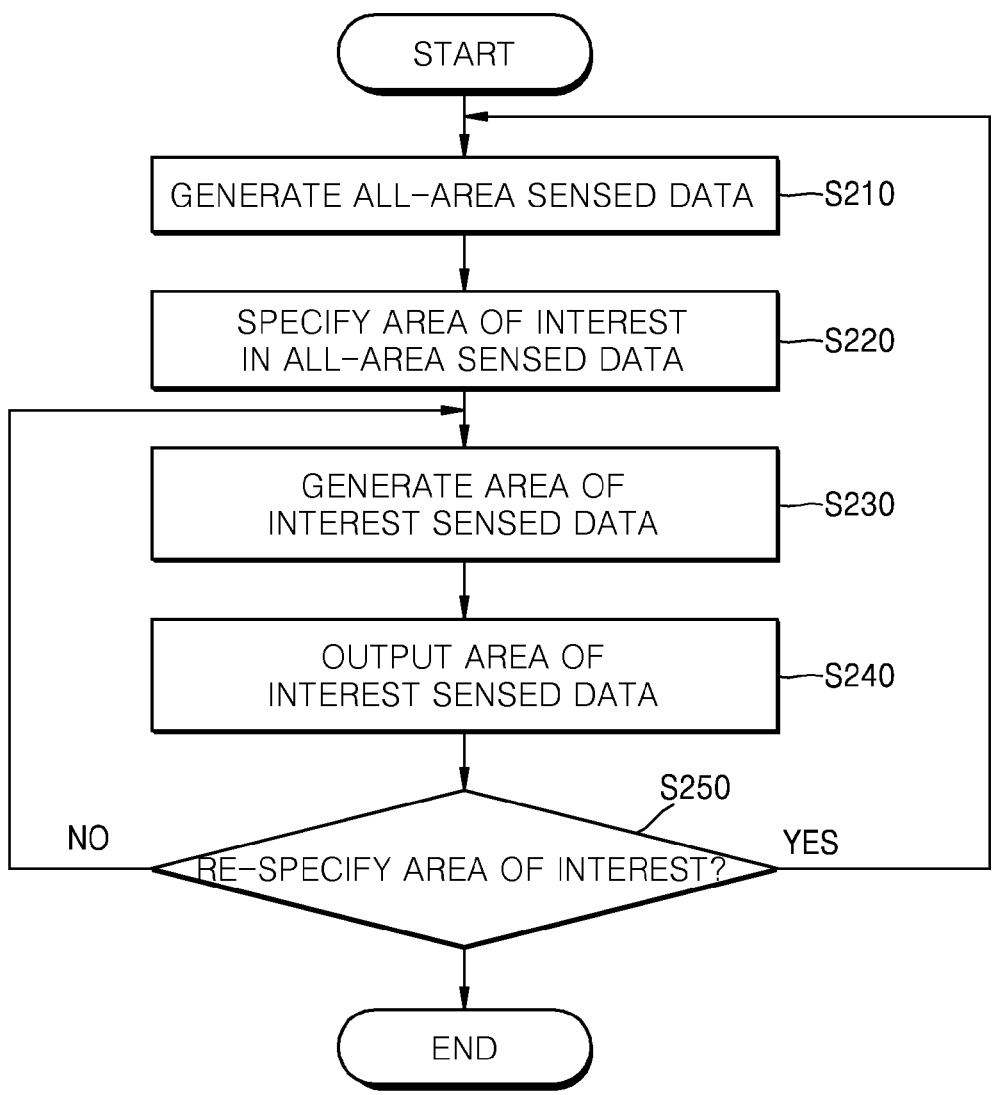
FIG. 2 is a flowchart showing a method of operating the cognitive sensor according to an example embodiment.

FIG. 2 is a flowchart illustrating a method of operating the cognitive sensor 100, according to an example embodiment.

Referring to FIGS. 1 and 2, the cognitive sensor 100 obtains all-area sensed data first (operation S210). In other words, the entire sensing elements 111 of the sensor unit 110 are driven and generate electric signals regarding outside stimulations, and the signal processing unit 140 receives the generated electric signals and generates all-area sensed data regarding the entire sensing elements 111. The generated all-area sensed data is transmitted to the cognitive circuit unit 150.

Next, according to at least one example embodiment, the cognitive circuit unit 150 specifies an area of interest among an entire image obtained from the transmitted all-area sensed data (operation S220). Such an area of interest may be determined based on environments or conditions under which the cognitive sensor 100 is operated. For example, if the cognitive sensor 100 according to at least one example embodiment is used to track a particular object, the particular object to be tracked becomes a target of interest, and the cognitive circuit unit 150 specifies an area of interest including the particular object to be tracked in the all-area sensed data. Here, the area of interest may be an area in which the particular object to be tracked is located or may include an area in which the particular object to be tracked is located, as well as areas adjacent to the particular object. For another example, if the all-area sensed data is an image including human faces and other background objects, a user's target of interest may be a human face, and the cognitive circuit unit 150 specifies an area of interest including human face in the entire image. For another example, if the all-area sensed data is an image including human irises and other background objects, a user's target of interest may be human irises, and the cognitive circuit unit 150 specifies an area of interest including human irises in the entire image. For another example, if the all-area sensed data is a CT image of a patient, a user's target of interest may be a particular affected part of the patient, and the cognitive circuit unit 150 may specify an area of interest including the particular affected part in the entire image.

Next, information regarding an area of interest specified by the cognitive circuit unit 150 is transmitted to the signal processing unit 140, and the signal processing unit 140 generates area of interest sensed data based on the specified area of interest (operation S230). The signal processing unit 140 may ignore signals from the plurality of sensing elements 111 corresponding to areas other than the area of interest, receive electric signals from only plurality of sensing elements 111 corresponding to the area of interest, and generates area of interest sensed data therefrom. In this case, data regarding the areas other than the area of interest may be replaced with existing data, null data, or dummy data with repeating meaningless values. Alternatively, the signal processing unit 140 may simplify processing of signals from sensing elements 111 corresponding to the remaining areas as compared to processing of signals from sensing elements 111 corresponding to an area of interest. In this case, data corresponding to the remaining areas other than the area of interest may be low resolution data of which resolution is lower than the resolution of data corresponding to the area of interest. Such a signal processing for generating area of interest sensed data generates less loads to the signal processing unit 140 as compared to a signal processing for generating all-area sensed data, less power is consumed, and signals may be processed quicker.

Area of interest sensed data generated by the signal processing unit 140 may be output to outside devices via the I/O unit 190 (operation S240). The area of interest sensed data output from the I/O unit 190 may be understood as raw data. Since the data amount of the output area of interest sensed data is smaller than the data amount of all-area sensed data, bottleneck phenomenon may be reduced or prevented during output of sensed data to outside devices, and signal processing loads of an external device may be reduced.

Re-specification of an area of interest may be selectively performed, or periodically performed, based on pre-set conditions (operation S250). If an occasion demands, an area of interest may be initially specified only for once. In a case where re-specification of an area of interest is performed for a plurality of number of times periodically or not periodically, the cognitive sensor 100 may perform an operation S210 for generating all-area sensed data periodically or not periodically and an operation S220 for specifying an area of interest in generated all-area sensed data. Sensed data output from the cognitive sensor 100 may sometimes or always be area of interest sensed data. Alternatively, area of interest sensed data generated periodically or not periodically may be output to outside devices via the I/O unit 190.

Although the example embodiments described above with reference to FIGS. 1 and 2 exemplify cases in which all of the sensing elements 111 of the sensor unit 110 are driven and the signal processing unit 140 processes area of interest sensed data based on an area of interest, the example embodiments are not limited thereto. As in the example embodiments described below, if each of the sensing elements 111 of the sensor unit 110 may be independently driven, or the sensing elements 111 of the sensor unit 110 may be driven by groups, information regarding an area of interest specified by the cognitive circuit unit 150 may be transmitted to a driving circuit (not shown) for driving the sensor unit 110, and only sensing elements 111 corresponding to the area of interest may be driven from among the sensing elements 111 of the sensor unit 110. As a result, the sensor unit 110 may transmit only detected signals corresponding to the area of interest to the signal processing unit 140.

Figure 3:
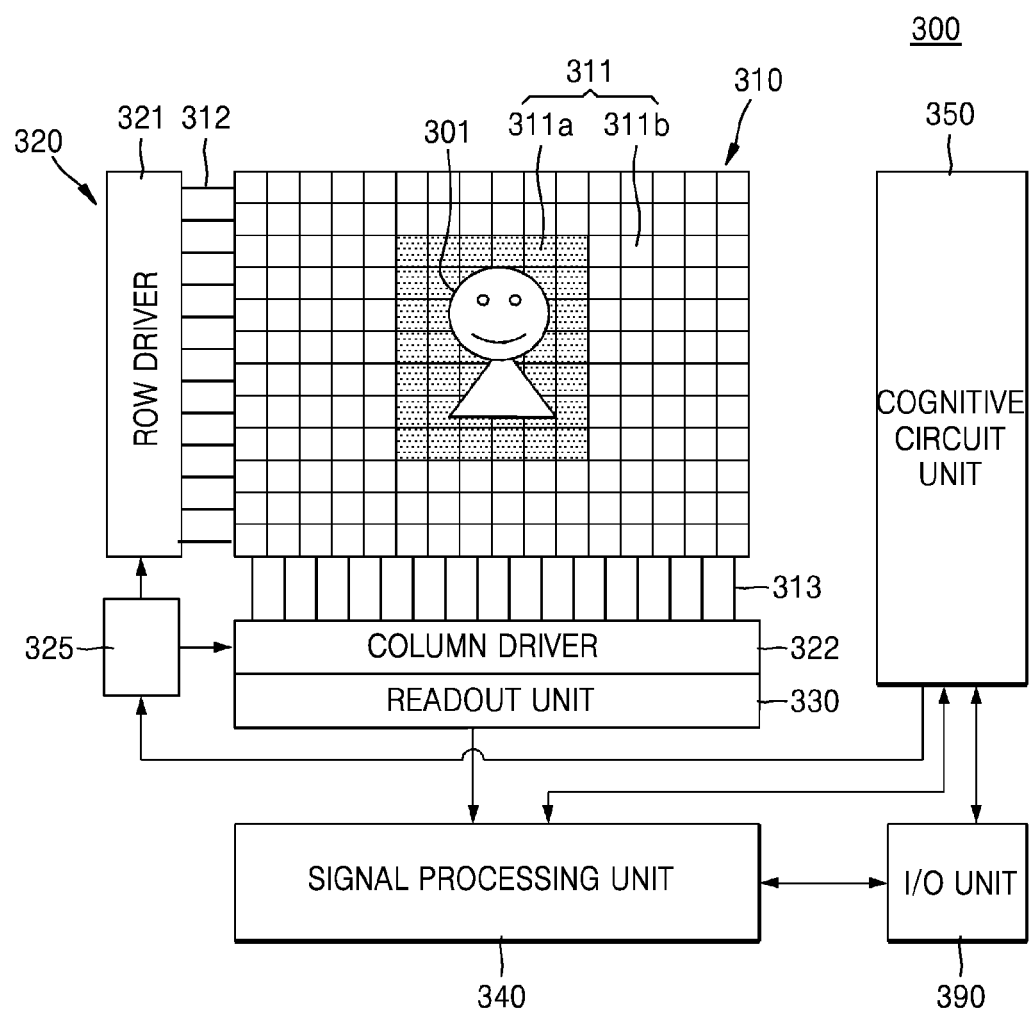
FIG. 3 is a schematic diagram showing the structure of a cognitive sensor according to another example embodiment.

FIG. 3 is a schematic diagram illustrating the structure of a cognitive sensor 300 according to another example embodiment.

Referring to FIG. 3, the cognitive sensor 300 according to the example embodiment is an image sensor for obtaining visual images and includes a pixel array 310, a driving circuit unit 320, a readout unit 330, a signal processing unit 340, a cognitive circuit unit 350, and an I/O unit 390. The pixel array 310, the driving circuit unit 320, the readout unit 330, the signal processing unit 340, the cognitive circuit unit 350, and the I/O unit 390 may constitute a single part by being integrated on a single chip and packaged together.

According to at least one example embodiment, the pixel array 310 is an area for converting a light into electric signals and generating pixel signals, that is, a sensor unit. In the pixel array 310, a plurality of pixels 311 are 2-dimensionally arranged. For example, the plurality of pixels 311 may be arranged in n rows and n columns. Each of the plurality of pixels 311 includes a photoelectric conversion element for converting a light into electric signals. For example, the photoelectric conversion element may be a photo diode or a photo conductor. Furthermore, each of the plurality of pixels 311 may include a pixel circuit for amplifying a pixel signal detected by the photoelectric conversion element. The pixel circuit may be substantially identical to a pixel circuit of a CMOS image sensor known in the art. For example, each of the plurality of pixels 311 may include a pixel circuit having a transfer transistor, a reset transistor, a selection transistor, and a source follower transistor.

According to at least one example embodiment, the driving circuit unit 320 is configured to generate control signals for controlling operation of the pixel array 310. For example, the driving circuit unit 320 may include a row driver 321, a column driver 322, and a timing generator 325. The row driver 321 may be configured to supply control signals (e.g., gate signals and source signals) to the pixels 311 of the pixel array 310 row-by-row via row lines 312. In other words, the row driver 321 may be configured to decode control signals output from the row driver 321 and to supply control signals to the pixels 311 of each of the rows of the pixel array 310. The pixels 311 in rows selected based on control signals output pixel signals to the readout unit 330 via column lines 313. The column driver 322 may be configured to generate a plurality of control signals under the control of the timing generator 325 and control operation of the readout unit 330. The timing generator 325 may be configured to control operations or timings of the row driver 321 and the column driver 322 by applying control signals or clock signals to the row driver 321 and the column driver 322. Circuits of the driving circuit unit 320 including the row driver 321, the column driver 322, and the timing generator 325 may be substantially identical to circuits of CMOS sensors known in the art, respectively.

The pixel array 310 may be configured to generate electric signals from an entire sensor area by driving all of the pixels 311 regularly or irregularly. Furthermore, the pixel array 310 may be configured to drive only pixels corresponding to an area of interest specified by the cognitive circuit unit 350 (referred to hereinafter as 'area of interest pixels 311a') and to generate only electric signals at the area of interest from among outside stimulations. In other words, when information regarding an area of interest is transmitted to the driving circuit unit 320, the timing generator 325 may be configured to generate control signals and clock signals to be supplied to the row driver 321 and the column driver 322 by using control signals and clock signals corresponding to the area of interest transmitted from the cognitive circuit unit 350. The row driver 321 and the column driver 322 control, such that only the area of interest pixels 311a are activated, that is, are in on-state in the pixel array 310. In the pixel array 310, remaining pixels 311b other than the area of interest pixels 311a are deactivated, that is, are in off-state.

The readout unit 330 may be configured to transmit pixels signals respectively generated by the plurality of pixels 311 to the signal processing unit 340. For example, if the driving circuit unit 320 is configured to control the pixel array 310 to output pixels signals from all of the pixels 311 of the pixel array 310 to the readout unit 330, the readout unit 330 is configured to transmit the pixel signals generated by all of the pixels 311 to the signal processing unit 340. If the driving circuit unit 320 is configured to control the pixel array 310 to output only pixels signals generated by the area of interest pixels 311a to the readout unit 330, the readout unit 330 is configured to transmit only the pixel signals generated by the area of interest pixels 311a to the signal processing unit 340. According to another example embodiment, the driving circuit unit 320 may be configured to drive part or all of the pixels 311 of the pixel array 310 and may be configured to control the readout unit 330 to transmit only pixel signals generated by the area of interest pixels 311a to the signal processing unit 340.

The signal processing unit 340 is configured to generate image data by processing pixel signals generated by the pixels 311 of the pixel array 310. The image data generated by the signal processing unit 340 may be either an all-area image data formed by processing pixel signals generated by all of the pixels 311 of the pixel array 310, or an area of interest image data formed by processing pixel signals generated by the area of interest pixels 311a corresponding to an area of interest specified by the cognitive circuit unit 350. In area of interest image data, data corresponding to areas other than the area of interest may be replaced with existing data or may be filled with null data or dummy data. Since such a signal processing for generating area of interest image data as described above inflicts less load to the signal processing unit 340 as compared to a signal processing for generating all-area image data, less power is consumed and signals may be processed quicker.

The cognitive circuit unit 350 is configured to receive all-area image data generated by the signal processing unit 340 and to specify an area of interest including a target of interest of a user. Such a cognitive circuit unit 350 may be embodied by an artificial intelligence technology known in the art, e.g., a neural network circuit or a neuromorphic circuit. The cognitive circuit unit 350 may be configured in advance to spatially and visually specify a target of interest of a user. Information regarding an area of interest specified by the cognitive circuit unit 350 may be transmitted to the driving circuit unit 320 and, as described above, only pixel signals from the area of interest pixels 311a may be output from the pixel array 310 to the readout unit 330.

The I/O unit 390 is configured to output image data generated by the signal processing unit 340 to outside devices (e.g., a display device, an information storage device, etc.) Control signals regarding the cognitive sensor 300 or information or programs for the cognitive circuit unit 350 to specify an area of interest may be received via the I/O unit 390. The I/O unit 390 may include an input unit an output unit that are integrated as a single circuit or separated from each other. Sensed data output from the cognitive sensor 300 may always be area of interest image data. Alternatively, all-area image data generated periodically or not periodically may also be output to outside via the I/O unit 390.

Next, a method of operating the cognitive sensor 300 according to an example embodiment will be described.

Figure 4:
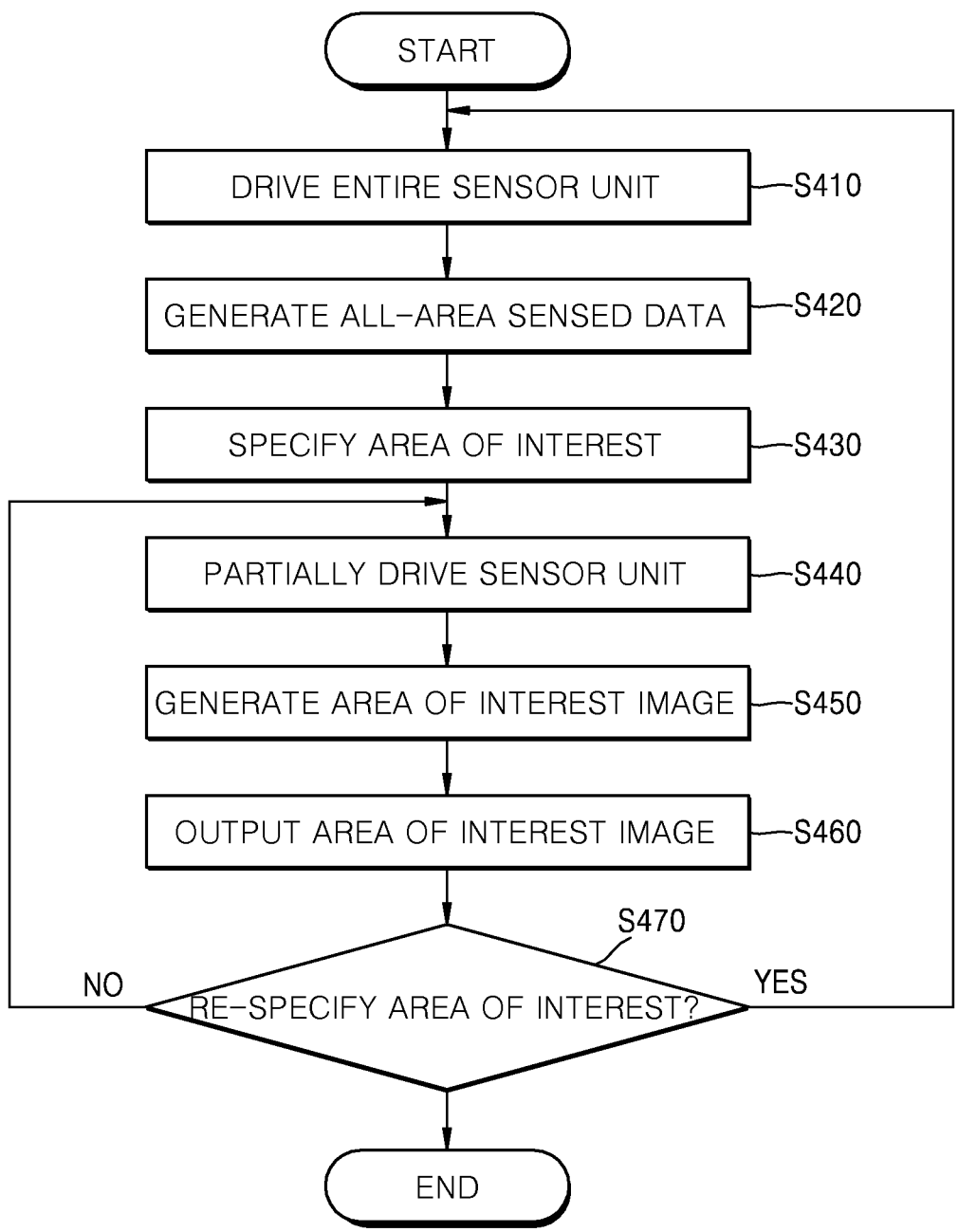
FIG. 4 is a flowchart showing a method of operating the cognitive sensor of FIG. 3.

FIG. 4 is a flowchart showing an example method of operating the cognitive sensor 300 of FIG. 3.

Referring to FIGS. 3 and 4, the cognitive sensor 300 drives all of the pixels 311 of the pixel array 310 first (operation S410). Signals obtained from the pixels 311 of the pixel array 310 are transmitted to the signal processing unit 340 via the readout unit 330, and the signal processing unit 340 generates all-area image data from the transmitted signals (operation S420). The generated all-area image data is transmitted to the cognitive circuit unit 350, and the cognitive circuit unit 350 specifies an area of interest in the all-area image data (operation S430). The term 'area of interest' may refer to an area including a target of interest in all-area image data. As described above, an area including a particular object corresponding to a target of interest (e.g., a face, an affected part, a target, etc.) (301 of FIG. 3) from among a plurality of objects constituting all-area image data may be an area of interest. Next, information regarding an area of interest specified by the cognitive circuit unit 350 is transmitted to the driving circuit unit 320, and the driving circuit unit 320 controls the pixel array 310, such that only the area of interest pixels 311a is activated, that is in on-state in the pixel array 310 (operation S440). Although a case in which all of the pixels 311 of the pixel array 310 are first driven at the beginning is described in the example embodiment, the example embodiments are not limited thereto. For example, when the cognitive sensor 300 begins to be driven, the operation S410 for driving all of the pixels 311, and the operation S420 for generating all-area image data may be omitted, information regarding an area of interest stored in a memory (not shown) of the cognitive circuit unit 350 may be transmitted to the driving circuit unit 320, and the driving circuit unit 320 may first drive only the area of interest pixels 311a of the pixel array 310 first based on the transmitted information regarding the area of interest.

Signals obtained from the area of interest pixels 311a of the pixel array 310 are transmitted to the signal processing unit 340 via the readout unit 330, and the signal processing unit 340 generates area of interest image data from the transmitted signals (operation S450).

According to at least one example embodiment, area of interest image data generated by the signal processing unit 340 is output to outside devices via the I/O unit 390 (operation S460). Image data output from the I/O unit 390 may be understood as raw data. At least a portion of such image data is area of interest sensed data. Of course, the I/O unit 390 may receive all-area image data regularly or irregularly from the signal processing unit 340, and output the all-area image data. Along with developments of semiconductor integration technologies, the number of the pixels 311 of the pixel array 310 is significantly increasing, and thus the size of all-area image data is also significantly increasing. The cognitive sensor 300 according to an example embodiment may significantly reduce signal processing load of the signal processing unit 340 by driving only the area of interest pixels 311a. As signal processing load of the signal processing unit 340 is reduced, the cognitive sensor 300 may pick up images faster or may consume less power. Furthermore, since the data amount of an output area of interest image data is smaller than the data amount of an all-area image data, bottleneck phenomenon may be reduced or prevented during output of data from the cognitive sensor 300 to outside devices, and signal processing loads of an external device may be reduced.

Re-specification of an area of interest may be selectively performed or periodically performed based on pre-set conditions (operation S250). If an occasion demands, an area of interest may be initially specified once.

Figure 5:
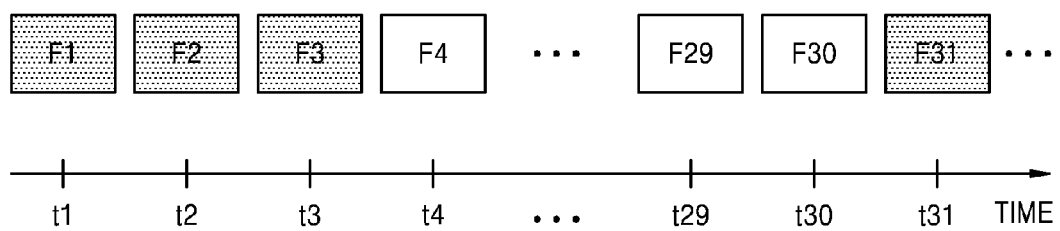
FIG. 5 is a diagram showing an example in which acquisition of all-area image data and specification of an area of interest are periodically performed, according to an example embodiment.

FIG. 5 is a diagram showing an example in which acquisition of all-area image data and specification of an area of interest are periodically performed. Referring to FIG. 5, the cognitive sensor 300 successively picks up moving pictures. Here, from among 30 frames, the cognitive sensor 300 may be set to obtain all-area image data by driving all of the pixels 311 with respect to the first 3 frames, specify an area of interest based on at least some of the 3 frames constituting the all-area image data, and obtain area of interest image data with respect to the other 27 frames. The cognitive sensor 300 may output the 3 frames constituting the all-area image data and the 27 frames constituting the area of interest image data. As an occasion demands, all-area image data obtained from the first 3 frames may be used only by the cognitive circuit unit 350 to specify an area of interest, and 30 frames of data output from the cognitive sensor 300 to outside may be entirely area of interest image data. The acquisition of all-area image data and the specification of an area of interest as described above may be periodically repeated, for example, every 30 frames. Of course, the number of frames is merely an example and may vary based on performance or operation environment of the cognitive sensor 300.

Figure 6:
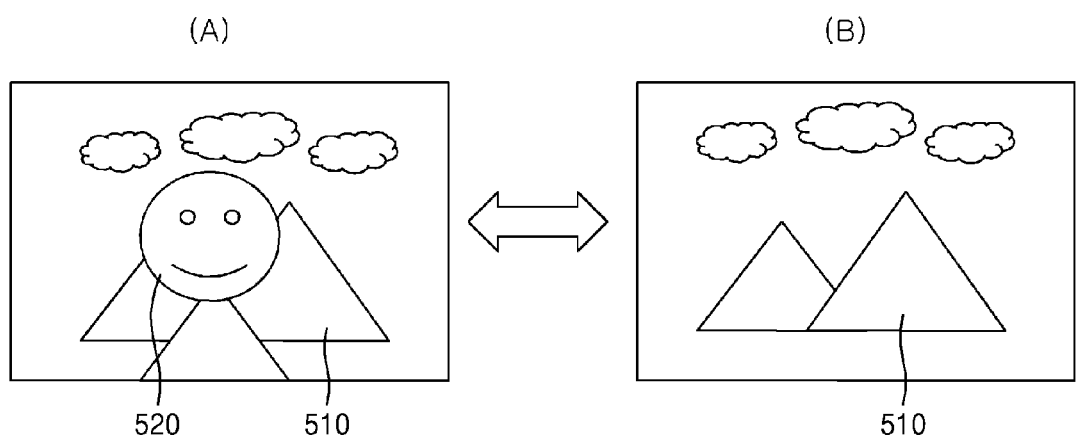
FIG. 6 is a diagram showing an example in which acquisition of all-area image data and specification of an area of interest are irregularly performed, according to an example embodiment.

FIG. 6 is a diagram showing an example in which acquisition of all-area image data and specification of an area of interest are irregularly performed. In FIG. 6, section (A) illustrates a scene in which a person 520 appears in a background 510, whereas section (B) illustrates a scene in which the person 520 disappeared and only the background 510 remains. In the scene shown in section (A) of FIG. 6, if a target of interest is the person 520, the cognitive sensor 300 may continuously output area of interest image data including the person 520. To recognize a case in which the scene shown in section (A) of FIG. 6 is switched to the scene shown in section (B) of FIG. 6, area of interest image data processed by the signal processing unit 340 may be periodically transmitted to the cognitive circuit unit 350. The person 520 disappears from area of interest images picked up by the cognitive sensor 300, and the cognitive circuit unit 350 may recognize such an irregular change of situation and re-specify an area of interest. It is not necessary for a change of situation for re-specifying an area of interest to be limited to a target of interest. For example, the cognitive circuit unit 350 may also re-specify an area of interest when the environment around a target of interest is partly or significantly changed. Alternatively, when the cognitive sensor 300 barely operates due to absence of a target of interest, and a target of interest suddenly appears as in a case where the scene shown in section (B) of FIG. 6 is switched to the scene shown in the section (A) of FIG. 6, the cognitive circuit unit 350 may also re-specify an area of interest.

Although the cognitive sensor 300 is a CMOS image sensor in the above-stated example embodiments, the example embodiments are not limited thereto. For example, the cognitive sensor 300 may also be applied to a CCD image sensor. Furthermore, although the cognitive sensor 300 is an image cognitive sensor for obtaining visual images in the above-stated example embodiments, the example embodiments are not limited thereto. In other words, a light sensed by the pixel array 310 of the cognitive sensor 300 is an example of outside stimulations, and the example embodiments are may also be applied to case where an outside stimulation is not a light (e.g., sound, contact, chemical substances, etc.).

Figure 7:
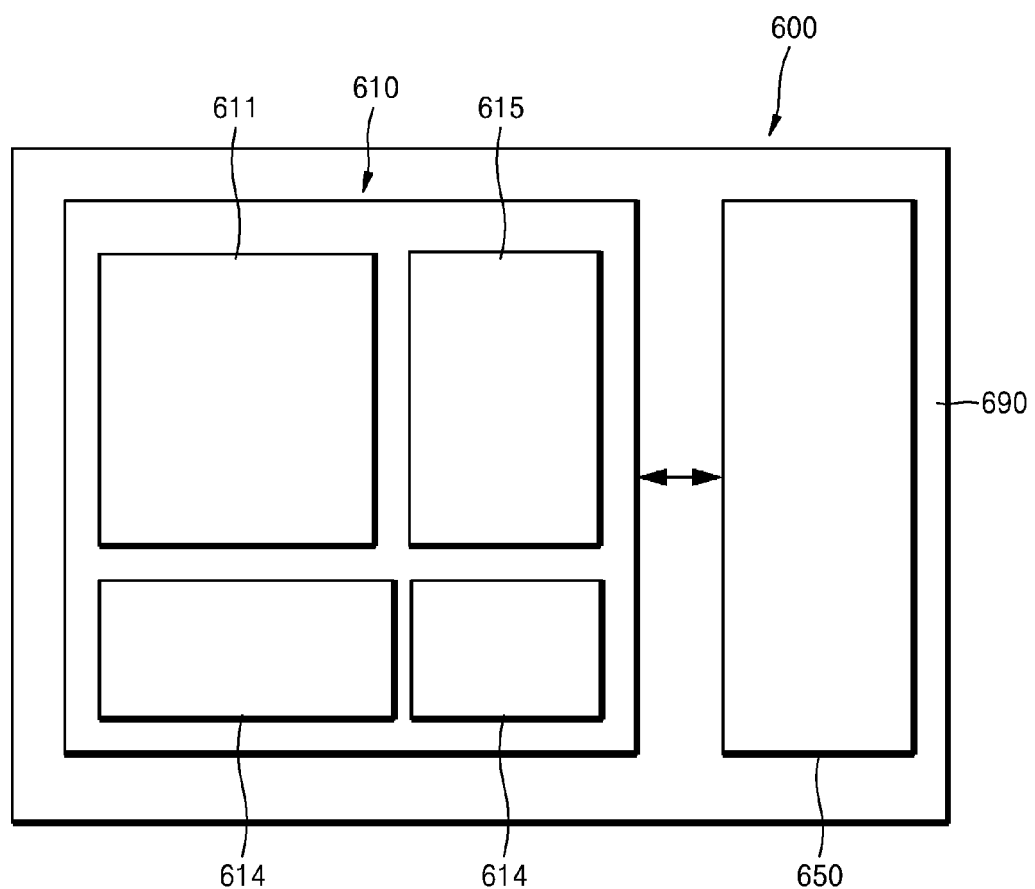
FIG. 7 is a diagram showing an example of a cognitive sensor according to another example embodiment.

FIG. 7 is a diagram showing an example of a cognitive sensor 600 according to another example embodiment. Referring to FIG. 7, the cognitive sensor 600 according to the example embodiment includes a first sensor 610 and a second sensor 620. The first sensor 610 may include a sensor unit 611, a signal processing unit 614, a cognitive circuit unit 615, and an I/O unit 619. The configuration of the first sensor 610 may be substantially identical to the configuration of the cognitive sensor 100 and the cognitive sensor 300 discussed above.

The second sensor 620 may be a sensor configured to obtain initial information for specifying an area of interest. The first sensor 610 may be, for example, an eye-tracking sensor or a motion sensor. For example, if the second sensor 620 is an eye-tracking sensor, the second sensor 620 may be configured to detect movements of pupils of a person and to transmit the detected information to the first sensor 610. For another example, if the second sensor 620 is a motion sensor, the second sensor 620 may be is configured to detect movement of an object, which is a target of interest, and to transmit the detected information regarding the target of interest to the first sensor 610. The first sensor 610 and the second sensor 620 may be inside a single housing 690. As an occasion demands, the second sensor 620 may be arranged outside the housing 690.

The cognitive circuit unit 615 of the first sensor 610 may be is configured to specify an area of interest in all-area sensed data transmitted from the signal processing unit 614 by using information regarding a target of interest transmitted from the second sensor 620 and to transmit information regarding the area of interest to the signal processing unit 614. The signal processing unit 614 may be is configured to generate area of interest sensed data based on the transmitted information regarding the area of interest, and the generated area of interest sensed data may be output via the I/O unit 619. If sensing elements of the sensor unit 611 may be independently driven, information regarding an area of interest specified by the cognitive circuit unit 615 may be transmitted to a driving circuit for driving the sensor unit 611 and only the sensing elements of the sensor unit 611 corresponding to the area of interest may be driven, as in the example embodiment described above with reference to FIGS. 3 and 4.

Figure 8:
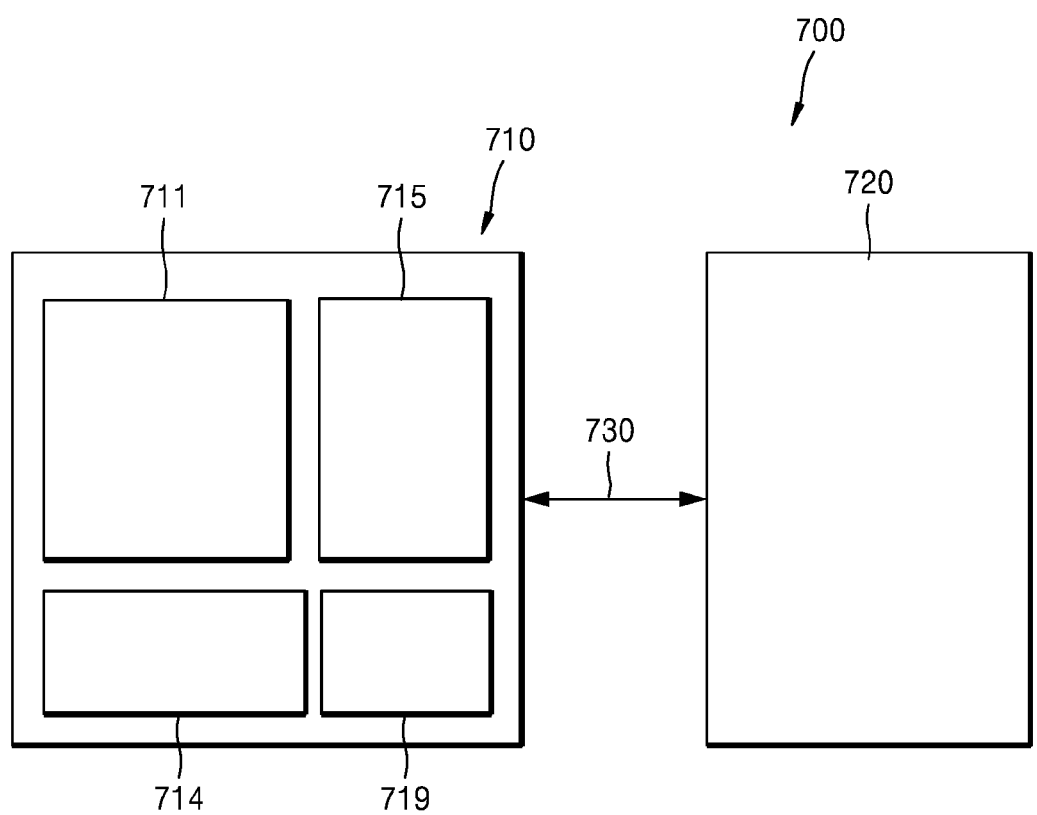
FIG. 8 is a schematic block diagram of a recognizing apparatus according to another example embodiment.

FIG. 8 is a schematic block diagram of a recognizing apparatus 700 according to another example embodiment. Referring to FIG. 8, the recognizing apparatus 700 includes a recognizing sensor 710 and a computing device 720. The recognizing sensor 710 includes a sensor unit 711, a signal processing unit 714, a cognitive circuit unit 715, and a I/O unit 719. The configuration of the recognizing sensor 710 may be substantially identical to the configuration of the cognitive sensor 100, the cognitive sensor 300, or the cognitive sensor 600 discussed above. The computing device 720 may be arranged outside the recognizing sensor 710. For example, the computing device 720 may be connected to the recognizing sensor 710 via a network 730. The network 730 may be a wired network or a wireless network, a local network or a wide area network, and does not limit the example embodiment.

To specify an area of interest, the cognitive circuit unit 715 of the recognizing sensor 710 may be is configured to transmit some information to the computing device 720, to receive information processed by the computing device 720, and to specify the area of interest in area of interest sensed data transmitted from the signal processing unit 714 by using information that is input or stored in advance, and information transmitted from the computing device 720. In other words, the cognitive circuit unit 715 may be is configured to specify an area of interest in conjunction with the computing device 720.

Although cases in which sensor units (or pixel arrays) of the cognitive sensors 100, 300, 600 and 700 include a plurality of sensing elements (or pixels), specifying areas of interest in spatial and visual images, and obtaining area of interest images only are described above, the example embodiments are not limited thereto. For example, even if a cognitive sensor includes only one sensing element and obtains sensed signals in chronological order, a cognitive circuit unit may specify a target of interest, process signals corresponding to the target of interest only, and output sensed data corresponding to the target of interest from an output end of the cognitive sensor as raw data.

According to the cognitive sensors and the method of operating the same of at least one example embodiment, signals received from a sensor unit may be filtered based on situations, relevant cognitive information may be spatially and visually confirmed, and only such information may be obtained.

According to the cognitive sensors and the method of operating the same of at least one example embodiment, sensing of information may focus on sensing of relevant cognitive information, thereby reducing signal processing loads in the cognitive sensor.

According to the cognitive sensors and the method of operating the same of at least one example embodiment, sensing of information may focus on sensing of relevant cognitive information, thereby improving sensing sensitivity or sensing performance.

It should be understood that the example embodiments described therein should be considered in a descriptive sense only and not for purposes of limitation. Descriptions of features within each example embodiment should typically be considered as available for other similar features in other example embodiments.

While one or more example embodiments have been described with reference to the figures, it will be understood by those of ordinary skill in the art that various changes in form and details may be made therein without departing from the spirit and scope of the example embodiments as defined by the following claims.

What is claimed is:

1. A recognition apparatus comprising:
a first cognitive sensor comprising:
a sensor unit configured to generate electric signals in response to outside stimulations;
a signal processing unit configured to generate sensed data regarding the outside stimulations by processing electric signals generated by the sensor unit;
a cognitive circuit unit of the first cognitive sensor configured to continuously specify an area of interest in the sensed data processed by the signal processing unit when a target is signaled in the sensed data and periodically specify the area of interest when the target is not signaled in the sensed area; and
an output unit configured to output the sensed data generated by the signal processing unit,
wherein at least a portion of the sensed data output by the output unit corresponds to the area of interest; and
a second sensor configured to obtain initial information for specifying an area of interest,
wherein the cognitive circuit unit of the first cognitive sensor is configured to specify the area of interest based on information obtained via the second sensor.

2. The recognition apparatus of claim 1, wherein the sensor unit, the signal processing unit, the cognitive circuit unit, and the output unit are integrated on a single chip.

3. The recognition apparatus of claim 1, wherein the signal processing unit is configured to replace data corresponding to areas other than the area of interest in the sensed data with existing data, null data, dummy data, or low-resolution data.

4. The recognition apparatus of claim 1, wherein the sensor unit comprises a sensing element array including a plurality of sensing elements, each of which being configured to convert outside stimulations into electric signals.

5. The recognition apparatus of claim 4, wherein the signal processing unit is configured to generate sensed data regarding outside stimulations corresponding to the area of interest by processing electric signals obtained from the sensing elements corresponding to the area of interest based on the area of interest specified by the cognitive circuit unit.

6. The recognition apparatus of claim 4, further comprising a driving circuit unit configured to drive the sensing element array,
wherein the driving circuit unit is configured to selectively drive sensing elements corresponding to the area of interest based on information regarding the area of interest received from the cognitive circuit unit.

7. The recognition apparatus of claim 6, wherein, while sensed data regarding outside stimulations corresponding to the area of interest is being generated, the driving circuit unit is configured to drive only sensing elements corresponding to the area of interest and to not drive the other sensing elements.

8. The recognition apparatus of claim 4, wherein one or more of the plurality of sensing elements comprises a photoelectric conversion element configured to convert a light into electric signals.

9. The recognition apparatus of claim 1, wherein the sensor unit is one of an ultrasound transducer configured to convert an ultrasound wave into electric signals, a tactile sensor configured to sense contact of a target object, a pressure sensor configured to sense a pressure from a target object, a bio-sensor configured to sense biological substances, and a chemical substance sensor configured to sense chemical substances.

10. The recognition apparatus of claim 1, wherein the cognitive circuit unit comprises a neural network circuit or a neuromorphic circuit.

11. The recognition apparatus of claim 10, wherein the cognitive circuit unit is configured to specify an area of interest in sensed data detected by the sensor unit based on prior information.

12. The recognition apparatus of claim 1, wherein the outside stimulations are one of an electromagnetic wave, a sound wave, a contact, a pressure, a biological substance, and a chemical substance.

13. The recognition apparatus of claim 1, wherein the second sensor comprises an eye-tracking sensor or a motion sensor.

14. A recognition apparatus comprising:
a first cognitive sensor including:
a sensor unit configured to generate electric signals in response to outside stimulations;
a signal processing unit configured to generate sensed data regarding the outside stimulations by processing electric signals generated by the sensor unit;
a cognitive circuit unit of the first cognitive sensor configured to continuously specify an area of interest in the sensed data processed by the signal processing unit when a target is signaled in the sensed data and periodically specify the area of interest when the target is not signaled in the sensed area; and
an output unit configured to output the sensed data generated by the signal processing unit,
wherein at least a portion of the sensed data output by the output unit corresponds to the area of interest;
a second sensor configured to obtain initial information for specifying an area of interest, and
a computing device, to which the first cognitive sensor is connected via a network,
wherein the cognitive circuit unit of the first cognitive sensor is configured to specify the area of interest in conjunction with the computing device based on information obtained via the second sensor.

15. A method of operating a recognition apparatus comprising a first cognitive sensor including a sensor unit which generates electric signals in response to outside stimulations, a signal processing unit which generates sensed data regarding the outside stimulations by processing electric signals generated by the sensor unit, a cognitive circuit unit of the first cognitive sensor which specifies an area of interest in the sensed data processed by the signal processing unit, and an output unit which outputs the sensed data generated by the signal processing unit, and a second sensor configured to obtain initial information for specifying an area of interest, the method comprising:
converting the outside stimulations into electric signals at the sensor unit;
continuously specifying the area of interest via the cognitive circuit unit when a target is signaled in the sensed data and periodically specifying the area of interest when the target is not signaled in the sensed area;
generating sensed data regarding the area of interest by processing electric signals corresponding to the area of interest from among the electric signals; and
outputting the sensed data generated by the signal processing unit via an input/output unit,
wherein at least a portion of the sensed data output by the output unit is sensed data regarding the area of interest, and wherein the cognitive circuit unit of the first cognitive sensor is configured to specify the area of interest based on information obtained via the second sensor.

16. The method of claim 15, wherein the signal processing unit replaces data corresponding to areas other than the area of interest in the sensed data with existing data, null data, dummy data, or low-resolution data.

17. The method of claim 15, further comprising recognizing a change of situation,
   wherein an area of interest is further specified based on information regarding the recognized change of situation.

18. The method of claim 15, wherein the sensor unit is a sensing element array including a plurality of sensing elements each of which being configured to convert outside stimulations into electric signals, and
   sensing elements corresponding to the area of interest from among the plurality of sensing elements are selectively driven, based on information regarding the area of interest received from the cognitive circuit unit.

* * * * *